(12) United States Patent
Koehler

(10) Patent No.: US 9,091,660 B2
(45) Date of Patent: Jul. 28, 2015

(54) DEVICE FOR MEASURING AT LEAST ONE PARAMETER OF AN ARTERIAL BLOOD SAMPLE

(75) Inventor: Hans Koehler, Graz (AT)

(73) Assignee: SMART MEDICAL SOLUTIONS GMBH, Graz (AT)

( * ) Notice: Subject to any disclaimer, the term of this patent is extended or adjusted under 35 U.S.C. 154(b) by 321 days.

(21) Appl. No.: 13/144,364

(22) PCT Filed: Jan. 12, 2010

(86) PCT No.: PCT/EP2010/050237
§ 371 (c)(1),
(2), (4) Date: Jul. 13, 2011

(87) PCT Pub. No.: WO2010/081789
PCT Pub. Date: Jul. 22, 2010

(65) Prior Publication Data
US 2011/0275913 A1 Nov. 10, 2011

(30) Foreign Application Priority Data
Jan. 13, 2009 (AT) .................................... A 46/2009

(51) Int. Cl.
*A61B 5/1455* (2006.01)
*G01N 21/77* (2006.01)
(Continued)

(52) U.S. Cl.
CPC .............. *G01N 21/77* (2013.01); *A61B 5/1427* (2013.01); *A61B 5/14546* (2013.01);
(Continued)

(58) Field of Classification Search
CPC ......................... A61B 5/1455; G01N 21/6428
USPC ................................................ 600/310–344
See application file for complete search history.

(56) References Cited

U.S. PATENT DOCUMENTS 4,215,940 A * 8/1980 Lubbers et al. ............... 356/402
4,830,013 A 5/1989 Maxwell
(Continued)

FOREIGN PATENT DOCUMENTS

EP 0809966 12/1997
JP 2003-535630 12/2003
(Continued)

OTHER PUBLICATIONS

Bizzarri et al., "Continuous oxygen monitoring in subcutaneous adipose tissue using microdialysis", Analytica Chimica Acta, Elsevier, DOI: 10.1016/J.Aca.2006.03.101, Jul. 28, 2006.
(Continued)

*Primary Examiner* — Eric Winakur
*Assistant Examiner* — Marjan Fardanesh
(74) *Attorney, Agent, or Firm* — RatnerPrestia

(57) ABSTRACT

The invention relates to a device for measuring at least one parameter of an arterial blood sample, including a flow sensor having standardized connecting elements which are connected to the inlet and the outlet side of a measuring cell of the flow sensor, the measuring cell having at least one optochemical sensor element which can be brought in contact with the blood sample. A connector is removably placed on the flow sensor and includes at least one light source for exciting the optochemical sensor element and at least one photodetector for receiving the measurement radiation of the optochemical sensor element. An electronic module has an electric connecting line to the connector and contacts the at least one light source and the at least one photodetector, the flow sensor being connectible to the standardized connection of an arterial catheter via the connecting element on the inlet side and to the standardized connection of an arterial infusion set via the connection on the outlet side.

14 Claims, 2 Drawing Sheets

(51) Int. Cl.
  *A61B 5/155* (2006.01)
  *A61B 5/145* (2006.01)
  *G01N 21/80* (2006.01)

(52) U.S. Cl.
  CPC ........ *A61B 5/14532* (2013.01); *A61B 5/14557* (2013.01); *G01N 21/7703* (2013.01); *G01N 21/80* (2013.01); *G01N 2021/7763* (2013.01)

(56)  References Cited

U.S. PATENT DOCUMENTS

| | | | |
|---|---|---|---|
| 4,989,606 A | | 2/1991 | Gehrich |
| 5,249,584 A | * | 10/1993 | Karkar et al. ................ 600/578 |
| 5,453,248 A | | 9/1995 | Olstein |
| 5,462,052 A | * | 10/1995 | Gehrich et al. ............... 600/323 |
| 5,871,627 A | * | 2/1999 | Abraham-Fuchs et al. .. 204/400 |
| 5,944,660 A | * | 8/1999 | Kimball et al. ............... 600/310 |
| 6,144,444 A | * | 11/2000 | Haworth et al. ............... 356/39 |
| 7,018,353 B2 | * | 3/2006 | Hunley et al. ................ 604/4.01 |
| 2001/0034479 A1 | * | 10/2001 | Ring et al. .................... 600/322 |
| 2006/0167405 A1 | * | 7/2006 | King et al. ..................... 604/65 |
| 2008/0097288 A1 | * | 4/2008 | Levin et al. .................... 604/66 |

FOREIGN PATENT DOCUMENTS

| | | |
|---|---|---|
| JP | 2006-521555 | 9/2006 |
| JP | 2009-000143 | 1/2009 |
| WO | WO 94/27495 | 12/1994 |
| WO | 9902084 | 1/1999 |
| WO | 0028322 | 5/2000 |
| WO | WO 01/94917 | 12/2001 |
| WO | WO 2004/085995 | 10/2004 |
| WO | WO 2008/150776 | 12/2008 |

OTHER PUBLICATIONS

International Search Report for PCT /EP2010/050237 mailed Apr. 29, 2010.

* cited by examiner

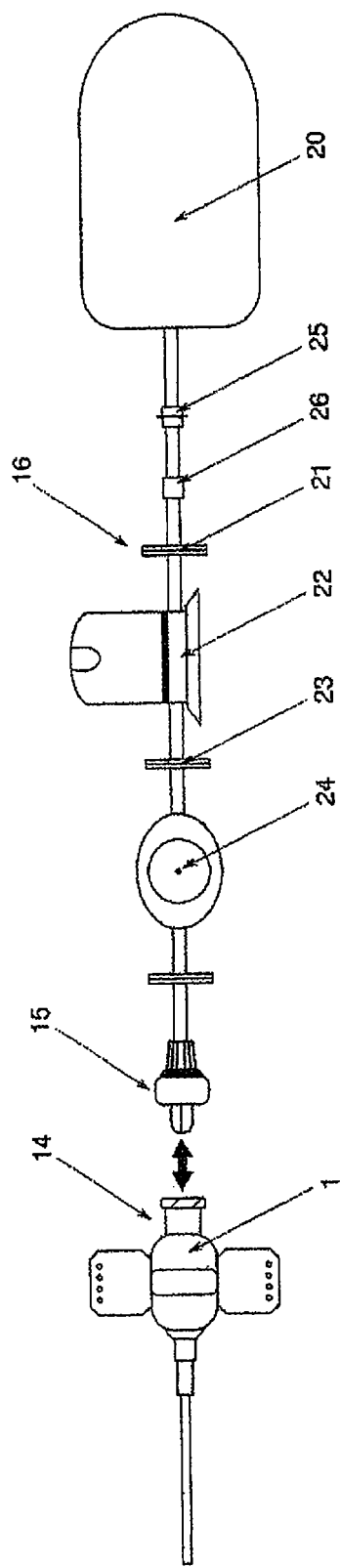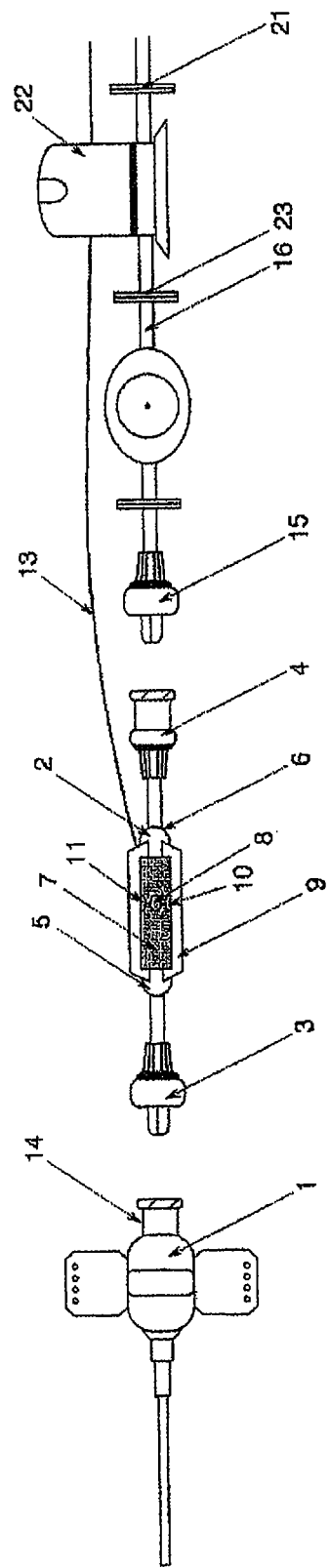

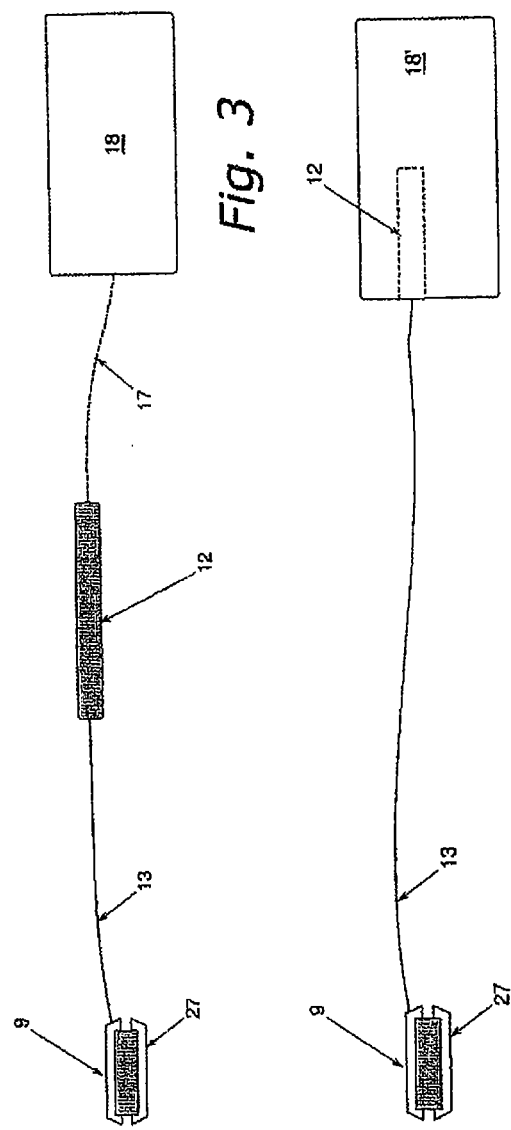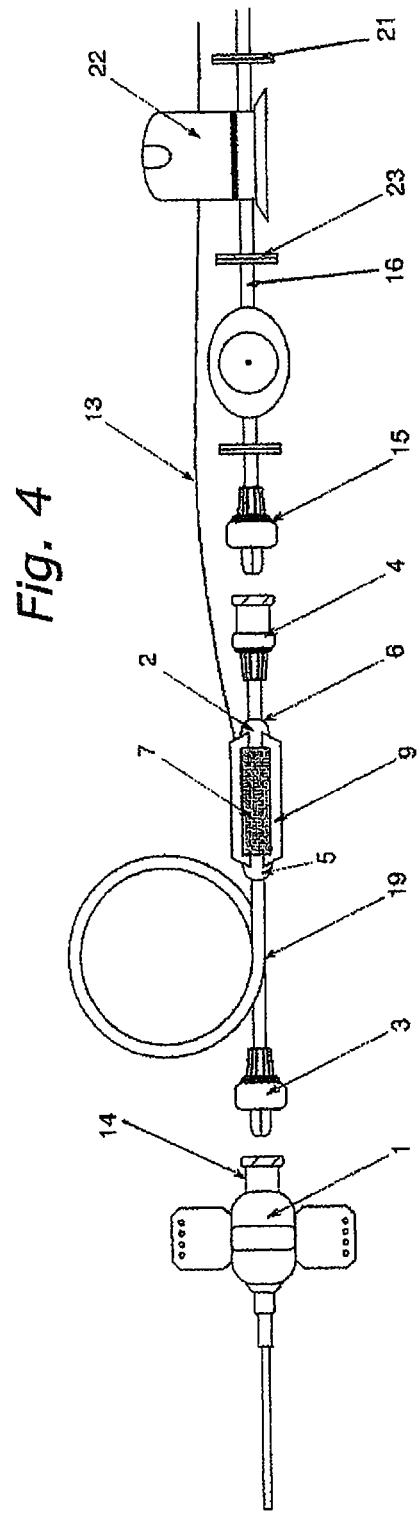

DEVICE FOR MEASURING AT LEAST ONE PARAMETER OF AN ARTERIAL BLOOD SAMPLE

CROSS REFERENCE TO RELATED APPLICATIONS

This application is the U.S. national phase application of PCT International Application No. PCT/EP2010/050237, filed Jan. 12, 2010, which claims priority to Austrian Patent Application No. A46/2009, filed Jan. 13, 2009, the contents of these applications being incorporated fully by reference herein.

FIELD OF THE INVENTION

The invention relates to a device for measuring at least one parameter of an arterial blood sample.

BACKGROUND OF THE INVENTION

To take a blood sample in an intensive care unit, for instance, when the patient has already been provided with an arterial access system, blood is manually aspired by means of an aspiration piston of the infusion set and withdrawn by means of a one-way syringe via the septum of the infusion set. The blood sample is then analysed in an external blood gas analyser or sent to a laboratory for analysis after transfer into a tubule. Withdrawal via the septum presents a certain risk of injury or infection for patient and personnel, and transport to the external blood gas analyser or sending to the laboratory may entail errors due to wrong labelling or confounding of samples.

DESCRIPTION OF RELATED ART

In this context it has become known to measure certain blood parameters directly on the patient. U.S. Pat. No. 4,989,606 A discloses an intravascular blood gas measuring system in which a tube communicating with the vascular system of the patient is directly connected to a sensor unit. The sensor unit comprises a flow-through sensor with fluorescence-optical sensors, for instance for measuring $O_2$ and $CO_2$ concentration and blood pH. On the outlet side of the flow-through sensor a tube is provided which connects to a pressurized bag containing a heparinized saline solution. The tube connected to the pressurized bag is provided with an adjustable drip valve and a manually actuated flushing valve.

The flow-through sensor of U.S. Pat. No. 4,989,606 A is held in a transmitter unit containing a thermostatting device for the blood sample and a number of light guides, which provide excitation radiation for the optical sensors and transmit the measured radiation. The whole sensor unit, which is attached to the patient's arm, is heavy and relatively bulky and frequently causes irritation when used. Moreover, the measuring system cannot be integrated into conventional infusion sets.

From EP 0 994 669 B1 a system for measuring blood parameters has become known, which may be used in an extracorporeal circulation system (heart-lung machine) during surgery. The system comprises a flow-through cartridge with a chamber receiving the blood sample, the cartridge containing at least one optical sensor. There is furthermore provided an apparatus for releasable connection of the cartridge, which contains a light source for exciting the sensor and a light detector for receiving the light emitted by the sensor and at least one signal transducer connected to the light detector. The signal transducer provides a digital output signal, which changes in accordance with the amount of light detected by at least one light detector. The disadvantages cited in the context of U.S. Pat. No. 4,989,606 will also prevail here, i.e. the device is bulky and cannot be integrated into conventional infusion sets.

Finally there is known from U.S. Pat. No. 4,830,013 A an intravascular measuring system for blood parameters, which comprises a catheter unit at whose distal end optical sensors for measuring blood gases ($O_2$- and $CO_2$-concentration, pH-value) are provided, each sensor sitting at the tip of a light guide.

SUMMARY OF THE INVENTION

An aspect of the present invention provides a device for measuring at least one parameter of an arterial blood sample, which has small volume and may easily be used with conventional arterial access systems.

According to aspects of the invention parameter measurement is achieved by an apparatus with the following components:
- a flow-through sensor with standardized connector fittings on the inlet and outlet side of the measuring cell of the flow-through sensor, the measuring cell containing at least one optochemical sensor element, which can be brought into contact with the blood sample,
- a connector, which is detachably plugged onto the flow-through sensor, containing at least one light source for excitation of the optochemical sensor element and at least one photodetector for receiving the measurement radiation of the optochemical sensor element,
- an electronic module with an electrical lead to the connector contacting the at least one light source and the at least one photodetector,
- where the flow-through sensor can connect via its connector fitting on the inlet side to the standardized fitting of an arterial catheter and via its connector fitting on the outlet side to the standardized fitting of an arterial infusion set.

A device according to aspects of the invention may be perfectly integrated in the clinical work procedure, since application of the measuring system only requires releasing of the standardized connection between arterial catheter and arterial infusion set and plugging-in of the system of the invention. The electronic module supplying power to the light sources and photodetectors in the connector, is connected to an evaluation and display unit via a flexible electrical lead, but could also be furnished with a wireless link, avoiding the necessity of a cable connection to the evaluation and display unit. The flow-through sensor together with the connector can be attached to the patient's arm, with the electronic module either also being attached to the arm or being integrated in the evaluation and display unit.

In an advantageous variant of the invention a preferably optical measuring element may be provided in the measuring cell of the flow-through sensor, which upon contact with the blood sample sends a starting signal to activate parameter measurement.

BRIEF DESCRIPTION OF THE DRAWINGS

The invention will now be described in more detail with reference to the enclosed drawings:
FIG. 1 is an illustration of an arterial access system including catheter and infusion set according to the state of the art;
FIG. 2 is an illustration of an embodiment of a device according to aspects of the invention for measuring at least one parameter of an arterial blood sample, which is integrated into an arterial access system such as shown in FIG. 1;

FIG. 3 and FIG. 4 are illustrations of different details of the device according to aspects of the invention as shown in FIG. 2; and FIG. 5 is an illustration of a preferred variant of the device of the invention as shown in FIG. 2.

DETAILED DESCRIPTION

A state-of-the-art arterial access system for taking a blood sample for blood analysis, has an arterial catheter 1 and an arterial infusion set 16 which may be directly plugged onto the catheter. At the outlet side of the infusion set there is a pressure bag 20 (schematically drawn) containing a heparinized flushing solution, for instance.

To carry out blood analysis a blood sample must be taken, which requires the following steps of procedure:
1. The stop valve 21 between the pressurized bag 20 and the aspiration piston 22 is closed.
2. A blood sample is manually aspired via the aspiration piston 22 of the infusion set 16.
3. The stop valve 23 between aspiration piston 22 and septum 24 for blood withdrawal is closed.
4. An arterial blood sample is withdrawn by means of a one-way syringe (not shown) via the septum 24. (Disadvantages: risk of infection for patient and personnel, risk of injury).
5. The blood sample is measured in an external analyser or transferred to tubules and sent to a laboratory for analysis. (Disadvantages: increased handling, danger of contamination).
6. The stop valve 23 is opened and the aspired blood is reinfused into the artery by means of the aspiration piston 22.
7. The septum 24 is cleaned.
8. The stop valve 21 is opened and the arterial line is cleaned via the flushing valve 26.

The manually adjustable drip valve of the infusion set is referred to as 25. The arterial catheter 1 and the infusion set 16 are provided with standardized fittings 14, 15, for instance Luer adaptors, by means of which the components 1 and 16 are connected so as to be fluid- and gas-tight in a well-known way.

In contrast to the above, the measuring system according to aspects of the invention as shown in FIG. 2 has advantages, since measuring the desired blood parameters will be carried out directly on the patient by means of a flow-through sensor 2, which is inserted between the standard components of an arterial access system, i.e. an arterial catheter 1 and an infusion set 16.

The flow-through sensor 2 of the device according to aspects of the invention has standardized connecting elements 3 and 4, for instance Luer adaptors, which connect to the inlet and outlet side 5, 6 of the measuring cell 7 of the flow-through sensor 2. In the measuring cell 7 there are located optochemical sensor elements 8, which can be brought into contact with the blood sample; in FIG. 2 only one such sensor element is shown schematically.

The device is furthermore provided with a connector 9, which can detachably be plugged onto the flow-through sensor 2 and is furnished with at least one light source 10 for excitation of the optochemical sensor element 8 and with a photodetector 11 for receiving the measuring radiation emitted by the sensor element 8. The measuring system can be operated at low cost, since the flow-through sensor can simply be exchanged when the device is to be used for a new measuring process.

As is further shown in FIG. 3, the connector 9 is connected via an electrical line 13 to an electronic module 12, which serves as a power supply for the light source 10 (e.g. a LED) and also passes on the signals of the photodetector 11 (e.g. a photodiode). The flow-through sensor 2 is connected via the connecting element 3 on the inlet side to the standardized fitting 14 of the arterial catheter 1 and via the connecting element 4 on the outlet side to the standardized fitting 15 of the arterial infusion set 16. The entire measuring system may thus be inserted into a commercially available arterial system as of FIG. 1 in a simple manner by opening the Luer connection.

The electronic module 12, which establishes electrical contact with the light sources 10 and the photodetectors 11 in the connector 9, communicates via an electrical line 17 or by a wireless link with an evaluation and display unit 18. As shown schematically in FIG. 4 the electronic module 12 may also be directly integrated in an evaluation and display unit 18'. The connector 9 is provided with a clamp 27, which grips the flow-through sensor in a stable way, such that the optical elements are held in a properly aligned fix.

In the variant of the device of the invention shown in FIG. 5 a flexible piece of tubing 19 is provided between the connecting element 3 on the inlet side of the flow-through sensor 2 and the measuring cell 7 proper, which relieves the mechanical load on the arterial catheter 1. Mechanical relief of this type may also be provided between the connecting element 4 on the outlet side and the measuring cell 7.

According to a variant of the invention a preferably optical measuring device may be provided in the measuring cell 7 of the flow-through sensor 2, which generates a starting signal to activate parameter measurement on contact with the blood sample. This device will also quickly detect blood which enters the sampling system by mistake, and will activate a corresponding optical or acoustical warning signal at the evaluation and display unit 18, 18' and initiate flushing of the catheter, if desired.

For blood analysis with the device of the invention only the following steps are performed:
1. Closing the stop valve 21 between pressure bag 20 and aspiration piston 22;
2. Manual aspiration of a blood sample by means of the aspiration piston 22 of the arterial infusion set 16. Following this, measurement may be automatically initiated by an optical blood detection device;
3. Waiting for a confirmation signal (acoustical or optical) of the evaluation and display unit 18 or 18' that measurement has been carried out;
4. Reinfusion of the blood sample by means of the aspiration piston 22;
5. Flushing the arterial lines by means of the flushing valve 26.

It is also possible to schedule measurements at predetermined time intervals by means of an automated system, aspiration of the blood sample into the measuring cell 7 of the flow-through sensor 2 being carried out by an automatically actuated piston- or peristaltic pump (not shown in the drawing).

According to aspects of the invention the measuring cell 7 of the flow-through sensor 2 may additionally be provided with a sensor for temperature measurement. Preferably the measurement is started only after the blood sample has come to rest. The automatic start of measurement may thus be coupled with a measurement of temperature. The flow rate or standstill of the blood sample may for instance be determined from the temperature gradient measured. The principle involved is that as long as the aspired blood moves the temperature will rise. When the blood in the measuring cell stops moving the temperature will begin to drop. The optimum starting point of measurement may thus be better determined and controlled, which will improve measurement accuracy.

Preferably the measuring cell 7 of the flow-through sensor is also provided with at least one sensor for measuring a parameter from the group $O_2$, $CO_2$, pH, sodium, potassium, glucose, lactate and temperature.

Advantages of the measurement system according to aspects of the invention include:

The measurement system may simply be integrated into a commercially available system of arterial catheter and arterial infusion set by means of standardized fittings (e.g. Luer connectors).

The device may thus be used with any conventional blood withdrawal system.

Use of the arterial catheter for all other desired applications may continue.

There is no infection risk for patient or personnel.

The measurement does not consume any blood.

There is no danger of confounding blood samples in the analysis process.

The invention claimed is:

1. A device for measuring at least one parameter of an arterial blood sample, the device comprising:
    a disposable flow-through sensor including a measuring cell configured to receive the arterial blood sample; wherein the measuring cell is detachably connected between an inlet standardized connecting element and an outlet standardized connecting element of the flow-through sensor;
    at least one optochemical sensor element within the measuring cell that contacts the arterial blood sample received by the measuring cell;
    a reusable connector, which can be detachably plugged externally onto the flow-through sensor including the measuring cell containing the at least one optochemical sensor element, the connector including at least one light source for excitation of the optochemical sensor element and at least one photodetector for receiving the measurement radiation of the optochemical sensor element, wherein the at least one light source and the at least one photodetector of the connector do not come in contact with the received arterial blood sample when the connector is plugged onto the flow-through sensor,
    an electronic module with an electrical connecting line to the connector, the module in contact with the at least one light source and the at least one photodetector,
    the inlet standardized connecting element coupled to an inlet side of the measuring cell for removable connection to a standardized fitting of an arterial catheter; and
    the outlet standardized connecting element coupled to an outlet side of the measuring cell for removable connection to a standardized fitting of an arterial infusion set.

2. The device according to claim 1, wherein the electronic module is provided with an electrical connecting line or with a wireless link to an evaluation and display unit.

3. The device according to claim 1, wherein the electronic module is integrated in an evaluation and display unit.

4. The device according to claim 1, wherein a piece of flexible tubing is provided between either the connecting element on the inlet side or the connecting element on the outlet side of the flow-through sensor and the measuring cell to relieve the arterial catheter from mechanical load.

5. The device according to claim 1, wherein the connector has a clamp which grips the flow-through sensor in a mechanically stable way.

6. The device according to claim 1, further comprising an optical measuring element in the measuring cell of the flow-through sensor, which on contact with the blood sample emits a starting signal for activating parameter measurement.

7. The device according to claim 6, wherein the optical measuring element is configured to generate a warning signal when the blood sample enters the flow-through sensor by mistake.

8. The device according to claim 1, further comprising a manually actuated aspiration piston of the arterial infusion set configured to aspirate the blood sample into the measuring cell of the flow-through sensor.

9. The device according to claim 1, further comprising an automatically actuated piston or peristaltic pump configured to aspirate the blood sample into the measuring cell of the flow-through sensor.

10. The device according to claim 1, wherein the measuring cell of the flow-through sensor additionally is provided with a sensor for temperature measurement.

11. The device according to claim 10, wherein the sensor for temperature measurement is configured to detect a rise in temperature based on the flow of the blood sample.

12. The device according to claim 11, wherein an automated system is configured to start measurement of the at least one parameter upon the sensor for temperature measurement detecting the rise in temperature.

13. The device according to claim 1, wherein the measuring cell of the flow-through sensor is provided with at least one sensor for measuring a parameter selected from the group consisting of $O_2$, $CO_2$, pH, sodium, potassium, glucose, lactate and temperature.

14. The device according to claim 1, wherein the connector further comprises a clamp configured to grip the flow-through sensor to align the at least one light source and the at least one photodetector of the connector with the optochemical sensor element within the measuring cell.

* * * * *